United States Patent [19]
Reiter

[11] Patent Number: 6,147,061
[45] Date of Patent: Nov. 14, 2000

[54] PHOSPHINATE BASED INHIBITORS OF MATRIX METALLOPROTEASES

[75] Inventor: Lawrence A. Reiter, Mystic, Conn.

[73] Assignee: Pfizer Inc., New York, N.Y.

[21] Appl. No.: 08/892,417

[22] Filed: Jul. 14, 1997

Related U.S. Application Data

[60] Provisional application No. 60/021,959, Jul. 18, 1996.

[51] Int. Cl.[7] .............................. A61K 31/66; C07F 9/28
[52] U.S. Cl. .............................................. 514/114; 564/15
[58] Field of Search ................................. 514/114; 564/15

[56] References Cited

U.S. PATENT DOCUMENTS 4,885,283  12/1989  Broadhurst et al. ...................... 517/78

FOREIGN PATENT DOCUMENTS

| 0497192 A2 | 5/1992 | European Pat. Off. . |
|---|---|---|
| 93/14112 | 7/1993 | WIPO . |
| 95/12603 | 5/1995 | WIPO . |

OTHER PUBLICATIONS

International Search Report–PCT/IB 97/00800, 1997.
Murphy et al., *Current Medicinal Chemistry*, 2, pp. 743–762 (1995).
Makonkawkeyoon, et al., *Proc. Natl. Acad. Sci.*, 90 (13), 5974 (1993).

*Primary Examiner*—Richard L. Raymond
*Assistant Examiner*—Pavanaram K Sripada
*Attorney, Agent, or Firm*—Peter C. Richardson; Paul H. Ginsburg; Elsa Djuardi

[57] ABSTRACT

A compound of the formula

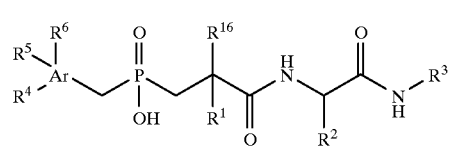

wherein $R^1$, $R^2$, $R^3$, $R^4$, $R^5$, $R^6$ and Ar are as defined above, useful in the treatment of a condition selected from the group consisting of arthritis, cancer, synergy with cytotoxic anti-cancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinim, etoposide, taxol, taxotere and other alkaloids, such as vincristine, in the treatment of cancer.

10 Claims, No Drawings

PHOSPHINATE BASED INHIBITORS OF MATRIX METALLOPROTEASES

This application claims benefit of U.S. Provisional Application Ser. No. 60/021,959 filed Jul. 18, 1996.

BACKGROUND OF THE INVENTION

The present invention relates to phosphinate based derivatives which are inhibitors of matrix metalloproteinases or the production of tumor necrosis factor (TNF) and as such are useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (hereinafter NSAID'S) and analgesics, and in combination with cytotoxic drugs such as adriamycin, daunomycin, cisplatinim, etoposide, taxol, taxotere and other alkaloids, such as vincristine, in the treatment of cancer.

This invention also relates to a method of using such compounds in the treatment of the above diseases in mammals, especially humans, and to pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.,* 52 (2): 244–248,1992).

Tumor necrosis factor is recognized to be involved in many infectious and auto-immune diseases (W. Friers, *FEBS Letters,* 1991, 285, 199). Furthermore, it has been shown that TNF is the prime mediator of the inflammatory response seen in sepsis and septic shock (C. E. Spooner et al., *Clinical Immunology and Immunopathology,* 1992, 62 S11).

SUMMARY OF THE INVENTION

The present invention relates to a compound of the formula

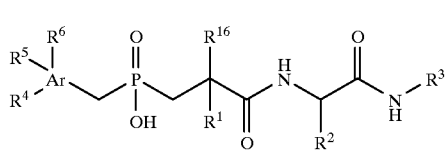

I or a pharmaceutically acceptable salt thereof; wherein

Ar is phenyl, pyridyl, pyrimidinyl, pyrazinyl, pyridazinyl, thienyl, furyl, pyrrolyl, oxazolyl, thiazolyl, isoxazolyl, isothiazolyl or imidazolyl;

$R^1$ and $R^{16}$ are each independently hydrogen, $(C_1-C_6)$ alkyl, $(trifluoromethyl)_2(C_1-C_6)$alkyl, perfluoro $(C_1-C_6)$alkyl, perfluoro$(C_1-C_6)$alkyl$(C_1-C_6)$alkyl, difluoromethoxy, trifluoromethoxy, $(C_3-C_7)$cycloalkyl $(C_1-C_6)$alkyl, $(C_6-C_{10})$aryl$(C_1-C_6)$alkyl, $(C_6-C_{10})$ aryloxy$(C_1-C_6)$alkyl or $(C_6-C_{10})$aryl$(C_1-C_6)$alkoxy $(C_1-C_6)$alkyl;

$R^2$ is $(C_1-C_6)$alkyl or $(C_6-C_{10})$aryl$(C_1-C_6)$alkyl optionally substituted by hydroxy, amino, halo, $(C_1-C_6)$alkyl, $(C_1-C_6)$alkoxy, $(trifluoromethyl)_2(C_1-C_6)$alkyl, perfluoro$(C_1-C_6)$alkyl, perfluoro$(C_1-C_6)$alkyl$(C_1-C_6)$ alkyl, difluoromethoxy, trifluoromethoxy, carboxy or carboxamoyl;

$R^3$ is $(C_1-C_6)$alkyl or $(C_6-C_{10})$aryl;

$R^4$ is hydrogen, $(C_1-C_6)$alkyl, $(C_1-C_6)$alkoxy, $(C_3-C_7)$ cycloalkyl$(C_1-C_6)$alkyl, $(C_1-C_6)$alkylsulfonyl, $(C_6-C_{10})$aryl, $(C_6-C_{10})$aryloxy, $(C_6-C_{10})$arylsulfonyl, $(C_6-C_{10})$aryl$(C_1-C_6)$alkyl, $(C_6-C_{10})$aryl $(C_1-C_6)$ alkoxy, $(C_6-C_{10})$aryl$(C_1-C_6)$alkylsulfonyl, N-phthalimido, $(C_6-C_{10})$arylNHCO, $(C_6-C_{10})$ arylNHSO$_2$, $R^7$OOC, $R^7R^8$NCO, $R^7R^8$NSO$_2$ wherein $R^7$ and $R^8$ are each independently hydrogen, $(C_1-C_6)$ alkyl or $(C_6-C_{10})$aryl$(C_1-C_6)$alkyl; $(C_1-C_6)$alkyl $CR^9R^{10}$, $(C_6-C_{10})$aryl $CR^9R^{10}$, $(C_6-C_{10})$aryl$(C_1-C_6)$ alkyl$CR^9R^{10}$ wherein $R^9$ and $R^{10}$ are each independently fluoro, $(C_1-C_6)$alkyl or $(C_1-C_6)$alkoxy;

or $R^9$ and $R^{10}$ may be taken together with the carbon to which they are attached to form a group of the formula

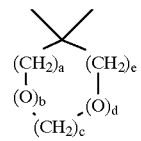

wherein a is 0, 1 or 2;

b is 0 or 1;

c is 1, 2, or 3;

d is 0 or 1; and e is 0, 1 or 2;

$R^5$ and $R^6$ are each independently hydrogen, $(C_1-C_6)$ alkyl, $(C_1-C_6)$alkoxy, halo, $(trifluoromethyl)_2(C_1-C_6)$ alkyl, perfluoro$(C_1-C_6)$alkyl, perfluoro$(C_1-C_6)$alkyl $(C_1-C_6)$alkyl, difluoromethoxy, trifluoromethoxy, $(C_1-C_6)$alkylthio, $(C_1-C_6)$alkylsulfinyl or $(C_1-C_6)$ alkylsulfonyl;

or $R^1$ and $R^{16}$ may be taken together with the carbon to which they are attached to form a $(C_3-C_7)$cycloalkyl group optionally substituted by $(C_1-C_6)$alkyl, $(C_1-C_6)$ alkoxy, $(C_6-C_{10})$aryl$(C_1-C_6)$alkyl, $(C_6-C_{10})$aryl $(C_1-C_6)$alkyl or $(C_6-C_{10})$aryloxy;

or $R^5$ and $R^6$, when attached to adjacent carbon positions, may be taken ether to form a group of the formula

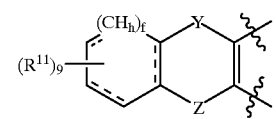

wherein the broken lines represent optional double bonds;

h is 1 or 2;

f and g are each independently 0, 1 or 2;

Y and Z are each independently $CH_2$, O, CO, SO$_2$, $CH_2CH_2$, $CH_2O$, $CH_2S$, $CH_2NH$, $CH_2CO$, $CH_2SO_2$, NHCO or NHSO$_2$; and $R^{11}$ is hydrogen, halo, $(C_1-C_6)$alkyl, $(C_1-C_6)$alkoxy, (trifluoromethyl)$_2(C_1-C_6)$alkyl, perfluoro$(C_1-C_6)$ alkyl, perfluoro$(C_1-C_6)$alkyl$(C_1-C_6)$alkyl, difluoromethoxy or trifluoromethoxy;

with the proviso that when either a or e is 0, the other must be 1;

with the proviso that when b and d are 1, the sum of a, c and e cannot be 5, 6 or 7;

with the proviso that when b and d are 0, the sum of a, c and e cannot be 7;

with the proviso that the methyene carbon attached to the phosphorus atom must be attached to a carbon atom of the Ar ring; and with the proviso that $R^5$ and $R^6$ must be attached to carbon atoms of the Ar ring.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The compound of formula I may have chiral centers and therefore exist in different enantiomeric forms. This invention relates to all optical isomers and stereoisomers of the compounds of formula I and mixtures thereof.

Preferred compounds of formula I include those wherein Ar is phenyl or thienyl.

Other preferred compounds of formula I include those wherein $R^1$ is 2-methylpropyl, trifluoromethylethyl, cyclopropylmethyl, cyclobutylmethyl, phenoxybutyl, cyclohexylmethyl, or phenylethyl.

Other preferred compounds of formula I include those wherein $R^2$ is $(C_1-C_6)$alkyl or 4-methoxybenzyl.

Other preferred compounds of formula I include those wherein $R^3$ is methyl.

Other preferred compounds of formula I include those wherein $R^4$ is benzyl, 2-chlorobenzyl, 2-fluorobenzyl, 3-fluorobenzyl or 4-fluorobenzyl.

More preferred compounds of formula I include those wherein Ar is phenyl or thienyl; $R^1$ is 2-methylpropyl, trifluoromethylethyl, cyclopropylmethyl, cyclobutylmethyl, phenoxybutyl, cyclohexylmethyl or phenylethyl; $R^2$ is $(C_1-C_6)$alkyl or 4-methoxybenzyl; $R^3$ is methyl and $R^4$ is benzyl, 2-chlorobenzyl, 2-fluorobenzyl, 3-fluorobenzyl or 4-fluorobenzyl.

Specific preferred compounds of formula I include the following:

(4-Benzylbenzyl)-[2-(2,2-dimethyl-1-methylcarbamoyl-propylcarbamoyl)-4-methylpentyl]-phosphinic acid;

(4-Benzylbenzyl-[2-(2,2-dimethyl-1-methylcarbamoyl-propylcarbamoyl)-5,5,5-trifluoropentyl]-phosphinic acid;

[2-(2,2-Dimethyl-1-methylcarbamoyl-propylcarbamoyl)-4-methylpentyl]-[4-(3-fluorobenzyl)-benzyl]-phosphinic acid;

Benzyl-{2-[2-(4-methoxyphenyl)-1-methylcarbamoyl-ethylcarbamoyl]-6-phenoxyhexyl}-phosphinic acid;

(4-Benzylbenzyl)-{2-[2-(4-methoxyphenyl)-1-methylcarbamoyl-ethylcarbamoyl]4-phenoxyhexyl}-phosphinic acid;

(4-Benzylbenzyl)-{3-cyclohexyl-2-[2-(4-methoxyphenyl)-1-methylcarbamoyl-ethylcarbamoyl]-propyl}-phosphinic acid;

(4-Benzylbenzyl)-[3-cyclohexyl-2-(2,2-dimethyl-1-methylcarbamoyl-propylcarbamoyl)-propyl]-phosphinic acid;

(4-Benzylbenzyl)-[2-(2,2-dimethyl-1-methylcarbamoyl-propylcarbamoyl)-4phenylbutyl]-phosphinic acid;

(4-Cyclohexylmethylbenzyl)-[2-(2,2-dimethyl-1-methylcarbamoyl-propylcarbamoyl)-4-methyl-pentyl]-phosphinic acid;

[2-(2,2-Dimethyl-1-methylcarbamoyl-propylcarbamoyl)-4-methylpentyl]-(4-isobutylbenzyl)-phosphinic acid;

[2-(2,2-Dimethyl-1-methylcarbamoyl-propylcarbamoyl)-4-methylpentyl]-[4-(4-fluoro-benzyl)-benzyl]-phosphinic acid;

[(2-(2,2-Dimethyl-1-methylcarbamoyl-propylcarbamoyl)-4-methylpentyl]-[4-(2-fluoro-benzyl)-benzyl]phophinic acid;

(4-Benzylbenzyl)-{2-[2-(4-methoxyphenyl)-1-methylcarbamoyl-ethylcarbamoyl]-4-methyl-pentyl}-phosphinic acid;

[4-(2-Chlorobenzyl)benzyl]-[2-(2,2-dimethyl-1-methylcarbamoyl-1-propylcarbamoyl)4-methylpentyl] phosphinic acid;

(5-Benzyl-pyridin-2-ylmethyl)-[2-(2,2-dimethyl-1-methylcarbamoyl-propylcarbamoyl)-4-methyl-pentyl] phosphinic acid;

[2-(2,2-Dimethyl-1-methylcarbamoyl-propylcarbamoyl)-5,5,5-trifluoro-pentyl]-[4-(2-fluoro-benzyl)-benzyl] phosphinic acid;

[3-Cyclopropyl-2-(2,2-dimethyl-1-methylcarbamoyl-propylcarbamoyl)-propyl]-[4-(2-fluoro-benzyl)-benzyl]phosphinic acid;

[3-Cyclobutyl-2-(2,2-dimethyl-1-methylcarbamoyl-propylcarbamoyl)-propyl]-[4-(2-fluoro-benzyl)-benzyl]-phosphinic acid; and (5-Benzyl-thiophen-2-ylmethyl)-[2-(2,2-dimethyl-1-methylcarbamoyl-propylcarbamoyl)-4-methylpentyl]-phosphinic acid.

The present invention also relates to a pharmaceutical composition for (a) the treatment of a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof effective in treating such a condition.

DETAILED DESCRIPTION OF THE INVENTION

The following reaction Schemes illustrate the preparation of the compounds of the present invention. Unless otherwise indicated $R^1$, $R^2$, $R^3$, $R^4$, $R^5$, $R^6$ and Ar in the reaction Schemes and the discussion that follow are defined as above.

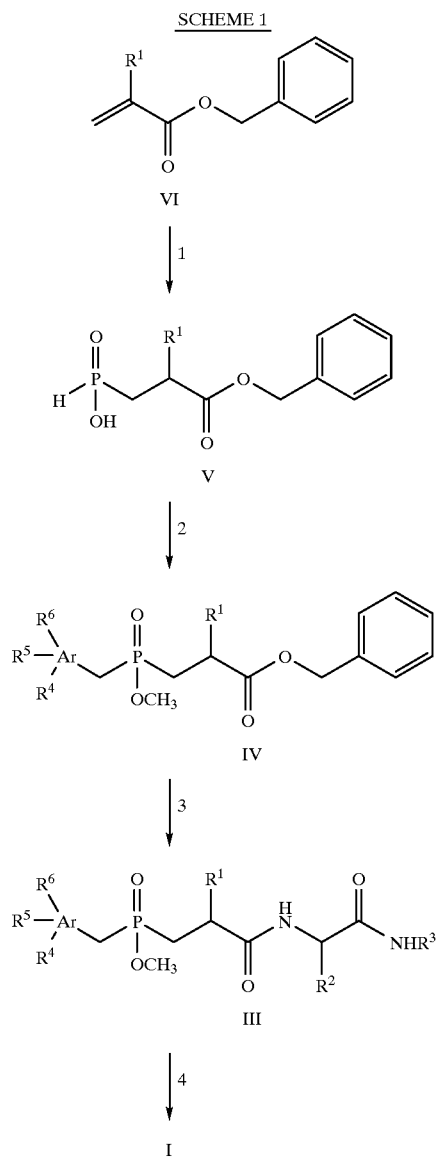

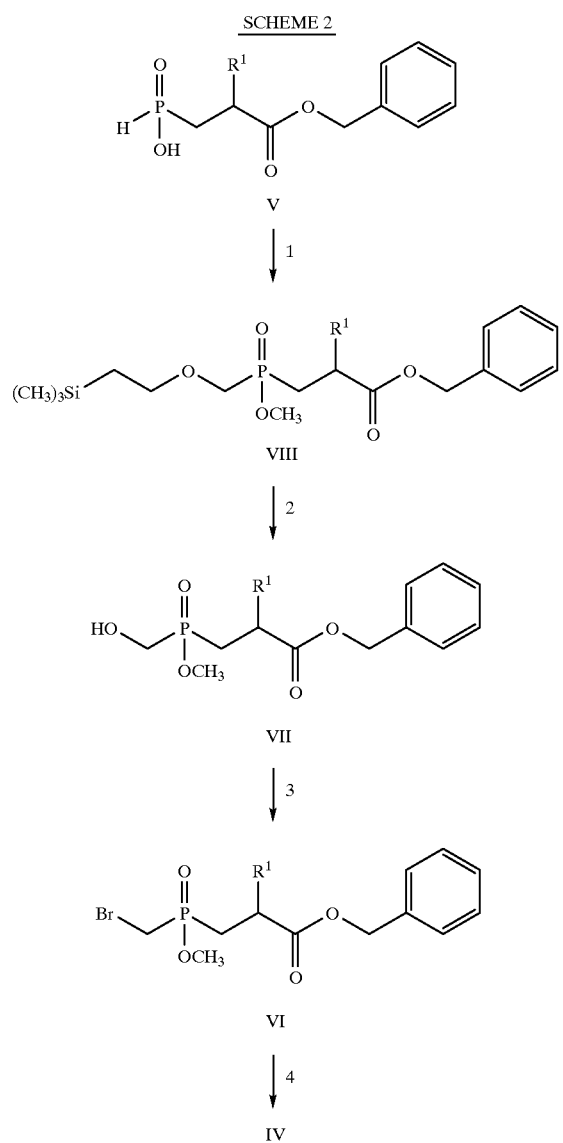

In reaction 1 of Scheme 1, the compound of formula VI is converted to the corresponding (2-benzyloxycarbonyl) phosphinic acid compound of formula V by reacting VI with bis-trimethylsilylphosphonite in an aprotic solvent, such as methylene chloride. The reaction mixture is stirred at room temperature for a time period between about 8 hours to about 48 hours, preferably about 18 hours.

In reaction 2 of Scheme 1, the compound of formula V is converted to the corresponding compound of formula IV by reacting V with an arylmethylhalide of the formula

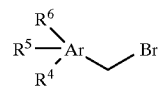

and N,O-bis(trimethylsilyl)acetamide in an inert aprotic solvent, such a methylene chloride. The reaction mixture is stirred at room temperature or heated to reflux for a time period between about 18 hours to about 72 hours, preferably about 24 hours. An excess of trimethylsilyidiazomethane in a 7:3 ratio mixture of toluene and methanol is then added to the crude reaction product so formed for a time period between about 15 minutes to about 2 hours, preferably about 30 minutes.

In reaction 3 of Scheme 1, the compound of formula IV is converted to the corresponding compound of formula III by (1) hydrogenating IV in the presence of a catalyst, such 5% palladium on barium sulfate, and a protic solvent, such as methanol, under a pressure between about 30 psi to about 60 psi, preferably about 45 psi, for a time period between about 15 minutes to about 3 hours, preferably about 1 hour, (2) reacting the intermediate so formed with hydroxysuccinimide and 2-diethylaminoethyl propyl carbodiimide hydrochloride in a polar aprotic solvent, such as dimethylformamide, at room temperature, for a time period between about 8 hours to about 48 hours, preferably about 20 hours, and (3) reacting the 2,5-dioxo-pyrrolidin-1-yl intermediate so formed with an amine of the formula

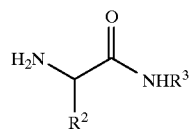

In an aprotic solvent, such as methylene chloride, at room temperature, for a time period between about 16 hours to about 48 hours, preferably about 18 hours.

In reaction 4 of Scheme 1, the compound of formula III is converted to the corresponding compound of formula I by treating III with 10% aqueous trifluoroacetic acid. The reaction mixture is stirred, at room temperature, for a time period between about 30 minutes to about 24 hours, preferably about 2 hours.

Scheme 2 presents an alternative method for preparing a compound of formula IV.

In reaction 1 of. Scheme 2, the compound of formula V is converted to the corresponding compound of formula VIII by reacting V with 2-(trimethylsilyl) ethoxymethyl chloride and N,O-bis(trimethylsilyl)acetamide in an inert aprotic solvent, such as methylene chloride. The reaction mixture is stirred at a temperature between about 20° C. to about 40° C., preferably about 25° C., for a time period between about 8 hours to about 48 hours, preferably about 18 hours. An excess of trimethylsilyldiazomethane in a 7:3 ratio mixture of toluene and methanol is then added to the crude reaction product so formed for a time period between about 15 minutes to about 2 hours, preferably about 30 minutes.

In reaction 2 of Scheme 2, the compound of formula VIII is converted to the corresponding compound of formula VII by reacting VIII with boron trifluoride diethyl etherate in a inert aprotic solvent, such as methylene chloride. The reaction mixture is stirred at a temperature between about 0° C. to about 40° C., preferably about 25° C., for a time period between about 1 hour to about 8 hours, preferably about 3 hours.

In reaction 3 of Scheme 2, the compound of formula VII is converted to the corresponding compound of formula VI by reacting VII with carbon tetrabromide in the presence of triphenylphosphine and diethyl azodicarboxylate in an inert aprotic solvent, such as methylene chloride. The reaction mixture is stirred at a temperature between about 0° C. to about 40° C., preferably about 25° C., for a time period between about 2 hours to about 24 hours, preferably about 4 hours.

In reaction 4 of Scheme 2, the compound of formula VI is converted to the corresponding compound of formula IV by reacting VI with an arylhalide of the formula

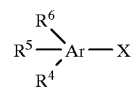

wherein X is bromo or iodo, in the presence of n-butyl lithium and copper (1) iodide in an inert aprotic solvent, such as tetrahydrofuran. The reaction mixture is stirred at a temperature between about −70° C. to about 60° C., preferably about 0° C., for a time period between about 1 hour to about 48 hours, preferably about 18 hours.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

BIOLOGICAL ASSAY

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 μM then the inhibitors are assayed at concentrations of 0.3 μM, 0.03 μM, 0.03 μM and 0.003 μM.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 μM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 ng/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 μM, then the inhibitors are assayed at final concentrations of 0.3 μM, 0.03 μM, 0.003 μM and 0.003 μM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 μl of a 10 mg/ml trypsin stock per 26 μg of stromelysin. The trypsin and stromelysin are incubated at 37° C. for 15 minutes followed by 10 μl of 10 mg/ml soybean trypsin inhibitor for 10 minutes at 37° C. for 10 minutes at 37° C. to quench trypsin activity.

Assays are conducted in a total volume of 250 μl of assay buffer (200 mM sodium chloride, 50 mM MES, and 10 mM calcium chloride, pH 6.0) in 96-well microliter plates. Activated stromelysin is diluted in assay buffer to 25 μg/ml. Ellman's reagent (3-Carboxy-4-nitrophenyl disulfide) is made as a 1M stock in dimethyl formamide and diluted to 5 mM in assay buffer with 50 μl per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM, and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2mM APMA (p-aminophenyl mercuric acetate) for 1.5 hours, at 37° C. and is diluted to 400 ng/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 ng/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys (NMA)-$NH_2$) is prepared as for inhibition of human collagenase (MMP-1) and 50 μl is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 μM, inhibitors are then assayed at final concentrations of 0.3 μM, 0.03 μM, 0.003 μM and 0.0003 μM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anticoagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flate bottom 96 well plates (Costar). Additions of compounds and LPS (100 ng/ml final concentration) gave a final volume of 200p1. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D ELISA Kit.

For administration to mammals, including humans, for the inhibition of matrix metalloproteinases or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration, e.g., for intramuscular, intraperitoneal, subcutaneous and intravenous use, a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The present invention is illustrated by the following examples, but it is not limited to the details thereof.

EXAMPLE 1

S,S and R,S (4-Benzylbenzyl)[2-(2,2-dimethyl-1-methylcarbamoyl propylcarbamoyl)-4-methylpentyl] phosphinic Acid Step A: 4-Benzoylbenzyl bromide (2.75 grams, 10.0 mmole) and triethylsilane (2.33 grams, 20 mmole) in trifluoroacetic acid (4.56 grams, 40 mmole) were warmed to 60° C. for 18 hours. The cooled mixture was diluted with ethyl acetate (50 ml) and carefully washed with saturated sodium bicarbonate solution (2×50 ml). After drying with magnesium sulfate, the extract was filtered and concentrated. The residue was chromatographed (0.5:99.5 to 2:98—ethyl acetate:hexane) to give 1.37 grams (52%) of 4-benzylbenzyl bromide as a colorless oil.

Step B: (2-Benzyloxycarbonyl-4-methylpentyl) phosphinic acid (1.14 grams, 4.0 mmole), 4-benzylbenzyl bromide (1.31 grams, 5.0 mmole) and N,O-bis (trimethylsilyl) acetamide (2.44 grams, 12 mmole) were combined in dry methylene chloride (40 ml); the mixture was degassed with a stream of dry nitrogen, then stirred at room temperature for 18 hours and refluxed for 24 hours. The cooled solution was quenched with 1N hydrochloric acid (25 ml). The methylene chloride layer was separated and washed with 1N hydrochloric acid (2×25 ml), dried with magnesium sulfate, filtered and concentrated to a turbid oil. This was dissolved in methanol (10 ml)/toluene (40 ml) and treated with excess trimethylsilyldiazomethane (commercial hexane solution). After 30 minutes the excess trimethylsilyldiazo-methane was destroyed with acetic acid. The solution was concentrated to an oil which was chromatographed (75:25—ethyl acetate:hexane) to give 1.18 grams (62%) of 2-[(4-benzylbenzyl) methoxyphosphinoylmethyl]-4-methylpentanoic acid benzyl ester as a colorless oil.

Step C: 2-[(4-Benzyl benzyl) methoxyphosphinoylmethyl]-4-methylpentanoic acid benzyl ester (650 mg, 1.36 mmole) was hydrogenated at 45 psi at room temperature in methanol (50 ml) over 5% palladium on barium sulfate (650 mg) for 1 hour. The catalyst was filtered off and washed with methanol. The filtrate was concentrated and traces of methanol removed by twice diluting the sample with methylene chloride and reconcentrating. The intermediate 2-[(4-benzyl benzyl) methoxyphosphinoylmethyl]-4-methylpentanoic acid was dissolved in dry dimethylformamide (14 ml) and hydroxysuccinimide (235 mg, 2.04 mmole) and dimethylaminopropylethylcarbodiimide hydrochloride (391 mg, 2.04 mmol) added. After stirring at room temperature for 20 hours the solution was diluted with ether (50 ml) and washed with 1N hydrochloric acid (50 ml, 2×25 ml) and saturated sodium bicarbonate solution (25 ml) and dried with magnesium sulfate. After filtration and concentration 566 mg (86%) of 2-[(4-Benzylbenzyl) methoxyphosphinoylmethyl]-4-methyl-pentanoic acid 2,5-dioxo-pyrrolidin-1-yl ester was obtained as an oil.

Step D: 2-[(4-Benzylbenzyl) methoxyphosphinoylmethyl]-4-methylpentanoic acid 2,5-dioxo-pyrrolidin-1-yl ester (120 mg, 0.25 mmole), (S)-2-amino-3,3,N-trimethylbutyramide hydrochloride (25 mg, 0.30 mmole) and diisopropylethylamine (39 mg, 0.30 mmole) were combined and stirred together for 18 hours at room temperature in dry methylene chloride (10 ml). Additional (S)-2-amino-3,3,N-trimethylbutyramide hydrochloride (25 mg, 0.30 mmole) and diisopropylethylamine (39 mg, 0.30 mmole) were added to the reaction mixture. After four days the solution was washed with 1N hydrochloric acid (2×10 ml) and saturated sodium bicarbonate solution (2×10 ml) and dried with magnesium sulfate. After filtration and concentration the residue was chromatographed (3:97—methanol:chloroform) to give 77 mg (60%) of (4-Benzylbenzyl)-[2-(2,2-dimethyl-1-methyl carbamoylpropylcarbamoyl)4-methylpentyl]-phosphinic acid methyl ester.

Step E: (4-Benzylbenzyl)-[2-(2,2-dimethyl-1-methyl carbamoylpropylcarbamoyl)-4-methylpentyl]-phosphinic acid methyl ester (77 mg, 0.15 mmole) was dissolved in 10% aqueous trifluoroacetic acid (6 ml). After 4 hours at room temperature the reaction mixture was concentrated. Residual water was removed by twice diluting the sample with toluene and reconcentrating to give 75 mg (100%) of the title compound as a hard glass which was a 63:37 mixture of S,S and R,S isomers, respectively. Mass spectrum m/e: $M^+ + 1$ 501, $M^+ + Na^+$ 523, $M^+ + K^+$ 540, $M^+ + 2Na^+$ 555. HPLC retention times: 13.00/15.90 minutes.

The compounds in Tables 1–4 were prepared by a method analogous to that described in in Example 1.

TABLE 1

Structure: A benzyl group with substituents $R^{12}$, $R^{13}$, $R^{14}$ connected via CH$_2$–P(=O)(OH)–CH$_2$–CH($R^1$)–C(=O)–NH–CH($R^2$)–C(=O)–NH–CH$_3$

| EX | $R^1$ | $R^2$ | $R^{12}$ | $R^{13}$ | $R^{14}$ | $R^1$ S/R | Ret. Time | MS |
|---|---|---|---|---|---|---|---|---|
| 2 | isobutyl | 4-methoxybenzyl | H | phenyl | H | 50/50 | 16.27/17.52 | LSIMS: 551 M$^+$ + HP + |
| 3 | isobutyl | 4-methoxybenzyl | phenyl | H | H | 52/48 | 16.48/17.74 | LSIMS: 551 M$^+$ + Na$^+$ 573 M$^+$ + Na$^+$ 589 M$^+$ + K$^+$ |
| 4 | isobutyl | 4-methoxybenzyl | H | H | phenyl | 51/49 | 13.70/15.13 | CI: 551 M$^+$ + H$^+$ 573 M$^+$ + Na$^+$ |
| 5 | isobutyl | 4-methoxybenzyl | H | H | methoxy | 59/41 | 5.91/8.36 | CI: 505 M$^+$ + H$^+$ |
| 6 | isobutyl | 4-methoxybenzyl | H | H | H | 49/51 | 7.03/9.42 | LSIMS: 475 M$^+$ + H$^+$ 497 M$^+$ + Na$^+$ |
| 7 | isobutyl | 4-methoxybenzyl | H | H | benzyl | 98/2 | 15.41/16.83 | LSIMS: 565 M$^+$ + H$^+$ |
| 8 | isobutyl | 4-methoxybenzyl | H | H | benzyl | 17/83 | 14.88/16.22 | LSIMS: 565 M$^+$ + H$^+$ |
| 9 | isobutyl | 4-methoxybenzyl | H | 1-phenyl-ethyl | H | 51/49 | 16.45/17.64 | LSIMS: 579 M$^+$ + H$^+$ |
| 10 | phenoxybutyl | 4-methoxybenzyl | H | H | H | 49/51 | 13.10/14.34 | LSIMS: 567 M$^+$ + H$^+$ 589 M$^+$ + Na + |
| 11 | phenoxybutyl | 4-methoxybenzyl | H | H | benzyl | 53/47 | 18.59/19.65 | LSIMS: 657 M$^+$ + H$^+$ |
| 12 | isobutyl | 4-methoxybenzyl | H | H | benzyl | 53/47 | 15.52/16.94 | |
| 13 | isobutyl | 4-methoxybenzyl | H | H | phenyl-sulfonyl | 50/50 | 10.36/11.94 | LSIMS: 615 M$^+$ + H$^+$ |
| 14 | isobutyl | 4-methoxybenzyl | H | H | phenoxy | 50/50 | 14.58/15.98 | LSIMS: 567 M$^+$ + H$^+$ |
| 15 | isobutyl | methyl | H | H | benzyl | 51/49 | 10.65/12.57 | LSIMS: 459 M$^+$ + H$^+$ 481 M$^+$ + Na + |
| 16 | cyclohexylmethyl | 4-methoxybenzyl | H | H | benzyl | 100:0 | 18.61/— | LSIMS: 605 M$^+$ + H$^+$ 627 M$^+$ + Na + |
| 17 | cyclohexylmethyl | 4-methoxybenzyl | H | H | benzyl | 19/81 | 18/55/19.92 | LSIMS: 605 M$^+$ + H$^+$ 627 M$^+$ + H$^+$ |
| 18 | isobutyl | tert-butyl | H | H | benzyl | 63/37 | 13.00/15.90 | LSIMS: 501 M$^+$ + H$^+$ 523 M$^+$ + Na + |
| 19 | cyclohexylmethyl | 4-methoxybenzyl | H | H | H | 50/50 | 12.00/13/59 | LSIMS: 515 M$^+$ + H$^+$ |
| 20 | cyclohexylmethyl | tert-butyl | H | H | benzyl | 56/44 | 16.48/19.64 | LSIMS: 541 M$^+$ + H$^+$ 563 M$^+$ + Na + |
| 21 | cyclohexylmethyl | tert-butyl | H | H | H | 66/34 | 9.11/13/08 | LSIMS: 451 M$^+$ + H$^+$ |
| 22 | cyclohexylmethyl | 4-methoxybenzyl | H | H | phenyl-sulfonyl | 49/51 | 1395/15/21 | LSIMS: 677 M$^+$ + Na + |
| 23 | cyclohexylmethyl | tert-butyl | H | H | phenyl-sulfonyl | 52/48 | 11.63/14/71 | LSIMS: 591 M$^+$ + H$^+$ |
| 24 | cyclohexylmethyl | methyl | H | H | phenyl-sulfonyl | 47/53 | 8.99/10.90 | LSIMS: 549 M$^+$ + H$^+$ 571 M$^+$ + Na + |
| 25 | isobutyl | methyl | H | H | H | 48/52 | 2.22/3.10 | CI: 369 M$^+$ 370 M$^+$ + H$^+$ |

TABLE 1-continued

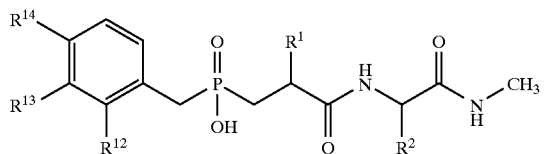

| EX | R$^1$ | R$^2$ | R$^{12}$ | R$^{13}$ | R$^{14}$ | R$^1$ S/R | Ret. Time | MS |
|---|---|---|---|---|---|---|---|---|
| 26 | isobutyl | tert-butyl | H | H | H | 51/49 | 10.05/11.63 | Cl: 411 M$^+$ + H$^+$ 428 M$^+$ + NH$_4$ +$^+$ |
| 27 | phenethyl | tert-butyl | H | H | H | 62/38 | 6.91/10.51 | Cl: 459 M$^+$ 460 M$^+$ +NH$_4^+$ |
| 28 | trans 4-methyl-cyclohexylmethyl | tert-butyl | H | H | H | 50/50 | 16.08/17.54 | Cl: 465 M$^+$ + H$^+$ 466 M$^+$ + 2 H$_4^+$ |
| 29 | trans 4-methyl cyclohexylmethyl | 4-methoxybenzyl | H | H | H | 50/50 | 14.54/15/91 | Cl: 529 M$^+$ + H$^+$ |
| 30 | trans 4-methyl-cyclohexylmethyl | methyl | H | H | H | 100/0 | 11.59/— | Cl: 530 M$^+$ + 2 H$^+$ |
| 31 | isobutyl | 4-methoxybenzyl | H | H | isobutyl | 50/50 | 15.85/17.45 | LSIMS: 423 M$^+$ + H$^+$ |
| 32 | isobutyl | tert-butyl | H | H | isobutyl | 50/50 | 13.46/16.64 | LSIMS: 531 M$^+$ + H$^+$ |
| 33 | isobutyl | methyl | H | H | isobutyl | 45/55 | 11.31/13.34 | LSIMS: 425 M$^+$ + H$^+$ 447 M$^+$ + Na + |
| 34 | isobutyl | tert-butyl | H | H | cyclohexyl methyl | 52/48 | 18.36/21.46 | LSIMS: 507 M$^+$ + H$^+$ |
| 35 | isobutyl | 4-methoxybenzyl | H | H | cyclohexyl methyl | 42/58 | 20.24/21.81 | LSIMS: 571 M$^+$ + H$^+$ |
| 36 | phenethyl | tert-butyl | H | H | benzyl | 50/50 | 15.30/17.53 | Cl: 549 M$^+$ + H$^+$ 550 M$^+$ + 2 H$^+$ |
| 37 | phenethyl | 4-methoxybenzyl | H | H | benzyl | 62/38 | 16.00/17.86 | Cl: 613 M$^+$ + H$^+$ 614 M$^+$ + 2 H$^+$ |
| 38 | phenethyl | methyl | H | H | benzyl | 3/97 | 12.94/14.34 | Cl: 507 M$^+$ + H$^+$ 508 M$^+$ + 2 H$^+$ |
| 39 | isopentyl | tert-butyl | H | H | benzyl | 53/47 | 14.92/17.69 | Cl: 515 M$^+$ + H$^+$ 516 M$^+$ + 2 H$^+$ |
| 40 | isopentyl | 4-methoxybenzyl | H | H | benzyl | 54/46 | 16.69/18.09 | Cl: 579 M$^+$ + H$^+$ 580 M$^+$ + 2 H$^+$ |
| 41 | cyclohexylethyl | tert-butyl | H | H | benzyl | 53/47 | 18.44/21.66 | Cl: 555 M$^+$ + H$^+$ |
| 42 | cyclohexylethyl | 4-methoxybenzyl | H | H | benzyl | 53/47 | 20.28/21.55 | Cl: 619 M$^+$ + H$^+$ |
| 43 | 3,3,3-trifluoropropyl | tert-butyl | H | H | benzyl | 47/53 | 13.01/15.03 | Cl: 540 M$^+$ 541 M$^+$ + H$^+$ |
| 44 | isobutyl | tert-butyl | H | H | 3-fluoro-benzyl | 53/47 | 12.67/15.56 | Cl: 519 M$^+$ + H$^+$ |
| 45 | isobutyl | tert-butyl | H | H | phenyl-CO— | 54/46 | 8.06/11.58 | Cl: 515 M$^+$ + H$^+$ 516 M$^+$ + 2 H$^+$ |
| 46 | propyl | tert-butyl | H | H | benzyl | 50/50 | 10.13/13.15 | Cl: 487 M$^+$ + H$^+$ |
| 47 | isobutyl | tert-butyl | H | H | 4-fluoro-benzyl | 48/52 | 12.85/15.59 | Cl: 519 M$^+$ + H$^+$ |
| 48 | isobutyl | tert-butyl | H | H | 2-fluoro-benzyl | 43/57 | 12.95/15.85 | Cl: 519 M$^+$ + H$^+$ |

TABLE 2

| EX | R$^1$ | R$^2$ | R$^{12}$ | R$^{13}$ | R$^{14}$ | R$^{15}$ | R$^1$ S/R | Ret. Time | MS |
|---|---|---|---|---|---|---|---|---|---|
| 49 | isobutyl | 4-methoxy-benzyl | H | H | benzylamino-carbonyl | H | 57/43 | 9.24/10.76 | LSIMS: 608 M$^+$ + H$^+$ |
| 50 | isobutyl | 4-methoxy-benzyl | H | H | methylamino-carbonyl | H | 48/52 | 15.35/16.68 | Cl: 532 M$^+$ + H$^+$ 538 M$^+$ + Li$^+$ |
| 51 | isobutyl | 4-methoxy-benzyl | benzylamino-carbonyl | H | H | H | 49/51 | 11.42/13.4 | LSIMS: 608 M$^+$ + H$^+$ 630 M$^+$ + Na$^+$ |
| 52 | isobutyl | 4-methoxy-benzyl | H | benzylamino-carbonyl | H | H | 47/53 | 09.74/11.44 | LSIMS: 608 M$^+$ + H$^+$ 630 M$^+$ + Na$^+$ |
| 53 | isobutyl | 4-methoxy-benzyl | H | H | dimethylamino-carbonyl | H | 34/66 | 10.77/12.64 | LSIMS: 546 M$^+$ + H$^+$ |
| 54 | isobutyl | 4-methoxy-benzyl | H | dimethylamino-carbonyl | H | H | 47/53 | 11.66/13.49 | LSIMS: 546 M$^+$ + H$^+$ |
| 55 | isobutyl | 4-methoxy-benzyl | H | H | benzyl(methyl)amino-carbonyl | H | 45/55 | 10.64/12.16 | LSIMS: 622 M$^+$ + H$^+$ |
| 56 | isobutyl | 4-methoxy-benzyl | H | benzyl(methyl)amino-carbonyl | H | H | 50/50 | 11.55/13.20 | LSIMS: 622 M$^+$ + H$^+$ 644 M$^+$ + Na$^+$ |
| 57 | isobutyl | 4-methoxy-benzyl | H | methoxy | benzylamino-carbonyl | CH$_3$O | 42/58 | 9.63/11.15 | LSIMS: 690 M$^+$ + Na$^+$ 712 M$^+$ + 2 Na$^+$ |
| 58 | isobutyl | 4-methoxy-benzyl | dimethylamino-carbonyl | H | H | H | 45/55 | 13.54/15.44 | LSIMS: 546 M$^+$ + H$^+$ 568 M$^+$ + 2 Na$^+$ |
| 59 | isobutyl | 4-methoxy-benzyl | benzyl(methyl)amino-carbonyl | H | H | H | 53/47 | 13.11/14.83 | LSIMS: 622 M$^+$ + H$^+$ |
| 60 | isobutyl | 4-methoxy-benzyl | H | methylamino-carbonyl | H | H | 46/54 | 10.02/12.09 | 532 M$^+$ + H$^+$ |
| 61 | isobutyl | tert-butyl | H | H | benzylamino-carbonyl | H | 50/50 | 3.88/6.54 | 566 M$^+$ + 2 Na$^+$ |

TABLE 3

| Ex | Y | Z | R$^1$ | R$^1$ S/R | Ret. Time | MS |
|---|---|---|---|---|---|---|
| 62 | —CH$_2$— | —CH$_2$CH$_2$— | isobutyl | 49/51 | 14.15/17.08 | Cl: 527 M$^+$ + H$^+$ |
| 63 | —CH$_2$— | —CH$_2$O— | isobutyl | 53/47 | 11.19/14.23 | Cl: 529 M$^+$ + H$^+$ |

TABLE 4

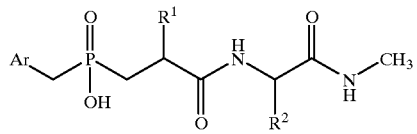

| EX | R¹ | R² | Ar | R¹ S/R | Ret. Time | MS |
|---|---|---|---|---|---|---|
| 64 | isobutyl | 4-methoxy-benzyl | 3-carbethoxy-2-pyridyl | 50/50 | 3.36/4.30 | LSIMS: 548 M⁺ + H⁺ |

EXAMPLE 65

S,S and R,S (4-Benzoylaminobenzyl)-{2-[2-(4-methoxyphenyl)-1-methylcarbamoylethylcarbamoyl]-4-methylpentyl}phosphinic Acid Step A: 2-[Methoxy(4-nitrobenzyl) phosphinoylmethyl]-4-methylpentanoic acid benzyl ester (prepared from 4-nitrobenzyl bromide and (2-benzyloxycarbonyl4-methylpentyl)phosphinic acid by the procedure described in Example 1/Step B) (900 mg, 2.08 mmole) in a mixture of ethanol (25 ml) and water (6 ml) was treated with concentrated hydrochloric acid (3 drops) and iron powder (1.14 grams, 20 mmole) at reflux. After 2 hours the cooled mixture was filtered through diatomaceous earth. The filtrate was concentrated and the residue chromatographed (ethyl acetate) to give 444 mg (53%) of 2-[(4-Aminobenzyl) methoxyphosphinoylmethyl]-4-methylpentanoic acid benzyl ester as a yellow oil.

Step B: 2-[(4-Aminobenzyl)methoxyphosphinoylmethyl] 4-methylpentanoic acid benzyl ester (230 mg, 0.57 mmole), benzoyl chloride (96 mg, 0.68 mmole), and triethylamine (69 mg, 0.68 mmole) were combined in cold (ice bath) chloroform (10 ml). After stirring for 1 hour at ice bath temperature the reaction mixture was diluted with chloroform (150 ml) and washed with water (20 ml), 1N hydrochloric acid (2×20 ml) and saturated sodium bicarbonate solution (2×20 ml) and dried with magnesium sulfate. After filtration and concentration the yellow residue was chromatographed (ethyl acetate) to give 190 mg (66%) of 2-[(4-Benzoylaminobenzyl)methoxy phosphinoylmethyl]4-methylpentanoic acid benzyl ester as a light yellow oil.

Step C: 2-[(4-Benzoylaminobenzyl)methoxy phosphinoylmethyl]-4-methylpentanoic acid benzyl ester (226 mg, 0.44 mmole) was hydrogenated hydrogenated at 50 psi at room temperature in methanol (20 ml) over 5% palladium on carbon (300 mg) for 2 hours. The catalyst was filtered off and washed with methanol. The filtrate was concentrated to give 154 mg (83%) of 2-[(4-benzoylaminobenzyl)methoxyphosphinoylmethyl]-4-methylpentanoic acid as an oil.

Step D: 2-[(4-Benzoylaminobenzyl)methoxyphosphinoyl methyl]-4-methylpentanoic acid (154 mg, 0.37 mmole), (S)-2-amino-3-(4-methoxyphenyl)-N-methylpropionamide (100 mg, 0.41 mmole), benzotriazol-1-yloxy -tris (dimethylamino)phosphonium hexafluorophosphate (180 mg, 0.41 mmole) and diisopropylethylamine (238 mg, 1.85 mmole) were stirred together in dry methylene chloride (10 ml) for 18 hours. The reaction mixture was concentrated and diluted with ethyl acetate (100 ml). This solution was washed with 1N hydrochloric acid (20 ml) and saturated sodium bicarbonate solution (20 ml) and dried with magnesium sulfate. Filtration and concentration gave the crude product which was purified by chromatography (10:90—methanol:methylene chloride) yielding 153 mg (68%) of (4-Benzoylamino benzyl){2-[2-(4-methoxyphenyl)-1-methylcarbamoylethylcarbamoyl]-4-methylpentyl}phosphinic acid methyl ester as a white solid.

Step E: By the procedure described in Example 1/Step E (4-Benzoylamino benzyl) {2-[2-(4-methoxyphenyl)-1-methylcarbamoylethylcarbamoyl]4methylpentyl} phosphinic acid methyl ester (153 mg, 0.25 mmole) was converted to 100 mg (67%) the title compound, a white solid which was a 50:50 mixture of S,S and R,S isomers, respectively. Mass spectrum m/e: M⁺+H⁺ 594, M⁺+Na⁺ 616. HPLC retention times: 8.32/10.33 minutes.

The compounds in Table 5 were prepared by a method analogous to that described in Example 65.

TABLE 5

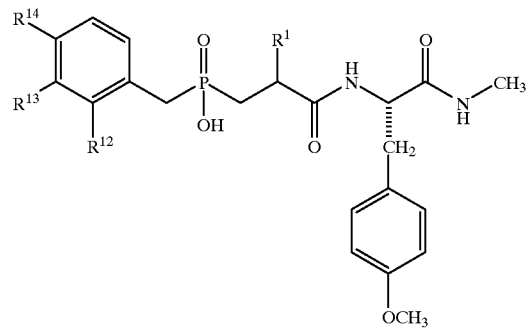

| EX | R¹ | R¹² | R¹³ | R¹⁴ | R¹ S/R | Ret. Time | MS |
|---|---|---|---|---|---|---|---|
| 66 | isobutyl | H | H | benzamido | 50/50 | 8.32/10.33 | LSIMS 594 M⁺ + H⁺ 616 M⁺ + Na⁺ |
| 67 | isobutyl | H | H | acetamido | 45/55 | 9.93/11.81 | 532 M⁺ + H⁺ 554 M⁺ + Na⁺ |

TABLE 5-continued

[Structure: R14, R13, R12-substituted benzyl-P(=O)(OH)-CH2-CH(R1)-C(=O)-NH-CH(CH2-C6H4-OCH3)-C(=O)-NH-CH3]

| EX | R¹ | R¹² | R¹³ | R¹⁴ | R¹ S/R | Ret. Time | MS |
|---|---|---|---|---|---|---|---|
| 68 | isobutyl | H | benzamido | H | 48/52 | 9.95/11.64 | 594 M⁺ + H⁺<br>616 M⁺ + Na⁺ |
| 69 | isobutyl | H | acetamido | H | 43/57 | 11.16/12.96 | 532 M⁺ + H⁺<br>554 M⁺ + Na⁺ |
| 70 | isobutyl | benzamido | H | H | 66/34 | 8.80/11.30 | 594 M⁺ + H⁺<br>616 M⁺ + Na⁺ |
| 71 | isobutyl | acetamido | H | H | 51/49 | 11.98/13.82 | 594 M⁺ + H⁺<br>616 M⁺ + Na⁺ |
| 72 | isobutyl | H | phenylsulfonyl-amino | H | 51/49 | 16.38/17.35 | 652 M⁺ + Na⁺ |

EXAMPLE 73

S,S and R,S [4-(1,3-Dioxo-1,3-dihydroisoindol-2-yl)benzyl]{2-[2-(4-methoxyphenyl)-1-methyl carbamoylethylcarbamoyl]-4-methylpentyl}phosphinic Acid Step A: 2-[(4-Aminobenzyl)methoxyphosphinoylmethyl]-4-methylpentanoic acid benzyl ester (prepared as described in Example 2/Step A) (242 mg, 0.60 mmole) and phthalic anhydride (133 mg, 0.90 mmole) in acetic acid (10 ml) were refluxed for 1 hour. The cooled reaction mixture was concentrated and the residue dissolved in ethyl acetate (100 ml). This solution was washed with saturated sodium bicarbonate solution (3×20 ml) and dried with magnesium sulfate. Filtration and concentration gave a light yellow oil which was purified by chromatography (ethyl acetate) yielding 162 mg (51%) of 2-{[4-(1,3-dioxo-1,3-dihydroisoindol-2-yl)benzyl]methoxyphosphinoyl methyl}-4-methylpentanoic acid benzyl ester as a yellow solid.

Step B: By the procedures described in Example 2/Steps C-E 2-{[4-(1,3-dioxo-1,3-dihydroisoindol-2-yl)benzyl]methoxyphosphinoyl methyl}-4-methylpentanoic acid benzyl ester (269 mg, 0.50 mmole) was converted to 61 mg (20%—3 steps) of the title compound, a white solid which was a 50:50 mixture of S,S and R,S isomers, respectively. Mass spectrum m/e: M⁺+H⁺ 620, M⁺+Na⁺ 642. HPLC retention times: 10.12/11.92 minutes.

The compounds in Table 6 were prepared by a method analogous to that described in Example 73.

TABLE 6

| EX | R¹ | R¹² | R¹³ | R¹⁴ | R¹ S/R | Ret. Time | MS |
|---|---|---|---|---|---|---|---|
| 74 | isobutyl | H | H | phthalimide | 50/50 | 10.12/11.92 | LSIMS:<br>620 M⁺ + H⁺<br>642 M⁺ + Na⁺ |

TABLE 6-continued

| EX | R$^1$ | R$^{12}$ | R$^{13}$ | R$^{14}$ | R$^1$ S/R | Ret. Time | MS |
|----|-------|----------|----------|----------|-----------|-----------|-----|
| 75 | isobutyl | H | phthalimide | H | 46/54 | 10.58/12.65 | LSIMS: 620 M$^+$ + H$^+$ 642 M$^+$ + Na$^+$ |
| 76 | isobutyl | phthalimide | H | H | 54/46 | 11.44/14.67 | LSIMS: 620 M$^+$ + H$^+$ 642 M$^+$ + Na$^+$ |

EXAMPLE 77

S,S and R,S (3-Aminobenzyl)-{2-[2-(4-methoxyphenyl)-1-methylcarbamoylethylcarbamoyl]-4-methylpentyl}phosphinic Acid Step A: {2-[2-(4-Methoxyphenyl)-1-methylcarbamoylethylcarbamoyl]-4-methyl-pentyl}-[3-(2,2,2-trifluoroacetylamino)benzyl]phosphinic acid methyl ester (prepared from the appropriate starting materials using the procedures described in Example 2/Steps A-D) (105 mg, 0.18 mmole) was treated with potassium carbonate (242 mg, 1.75 mmole) in 10% aqueous methanol (10 ml) for 18 hours. 1N Sodium hydroxide (1 ml) was added and after 3 hours the reaction mixture was concentrated and ethyl acetate (25 ml) and water (5 ml) added. The ethyl acetate layer was removed and the water extracted with ethyl acetate (3×20 ml). The combined ethyl acetate extracts were dried with magnesium sulfate and filtered. The filtrate was concentrated to give 56 mg (64%) of (3-aminobenzyl){2-[2-(4-methoxy phenyl)-1-methylcarbamoylethyl carbamoyl]-4-methylpentyl}phosphinic acid methyl ester as a light yellow oil.

Step B: By the procedure described in Example 1/Step E (3-aminobenzyl) {2-[2-(4-methoxy phenyl)-1-methylcarbamoylethyl carbamoyl]-4-methylpentyl}phosphinic acid methyl ester (56 mg, 0.11 mmole) was converted to 40 mg (74%) of the title compound, a white solid which was a 44:56 mixture of S,S and R,S isomers, respectively. Mass spectrum m/e: M$^+$+H$^+$ 490. HPLC retention times (20% to 80% gradient): 6.17/8.94 minutes.

EXAMPLE 78

S,S and R,S (3-Benzylaminobenzyl)-{2-[2-(4-methoxyphenyl)-1-methylcarbamoylethylcarbamoyl]-4-methylpentyl}phosphinic Acid Step A: (3-Aminobenzyl){2-[2-(4-methoxyphenyl)-1-methylcarbamoyl ethylcarbamoyl]-4-methylpentyl}phosphinic acid methyl ester (prepared as described in Example 4/Step A) (150 mg, 0.30 mmole), benzaldehyde (38 mg, 0.36 mmole), sodium cyanoborohydride (23 mg, 0.357 mmole) and acetic acid (1 drop) in methanol were stirred at room temperature for 3 hours. The reaction was quenched with 1N hydrochloric acid (few ml's) and the reaction mixture concentrated. The residue was dissolved in ethyl acetate (20 ml) and washed with 1N hydrochloric acid (20 ml), saturated sodium bicarbonate solution (20 ml) and dried with magnesium sulfate. Filtration and concentration gave the crude product which was purified by chromatography (3:97—methanol:methylene chloride) yielding 133 mg (75%) of (3-Benzylamino benzyl)-{2-[2-(4-methoxyphenyl)-1-methylcarbamoylethylcarbamoyl]-4-methylpentyl}phosphinic acid methyl ester as an oil.

Step B: By the procedure described in Example 1/Step E (3-Benzylamino benzyl)-{2-[2-(4-methoxyphenyl)-1-methylcarbamoylethylcarbamoyl]-methylpentyl} phosphinic acid methyl ester (133 mg, 0.22 mmole) was converted to 100 mg (64%) of the title compound, a white solid which was a 67:33 mixture of S,S and R,S isomers, respectively. Mass spectrum m/e: M$^+$+H$^+$ 580, M$^+$+Na$^+$ 602. HPLC retention times: 7.29/9.61 minutes.

EXAMPLE 79

Separation of S,S and R,S (4-benzylbenzyl)[2-(2,2-dimethyl-1-methylcarbamoylpropylcarbamoyl)-4-methylpentyl]phosphinic Acid A mixture of S,S and R,S (4-benzylbenzyl)[2-(2,2-dimethyl-1-methylcarbamoylpropylcarbamoyl)-4-methylpentyl]phosphinic acid (prepared as described in Example 1) (609 mg) was chromatographed on a preparative reverse phase (C-18) column eluting first with 40% aqueous acetonitrile containing 0.1% trifluoroacetic acid and then with 50% aqueous acetonitrile containing 0.1% trifluoroacetic acid. This gave nearly complete separation of the two diastereomers. Concentration of the fractions containing the two pure components gave 304 mg of S,S (4-benzylbenzyl)[2-(2,2-dimethyl-1-methylcarbamoyl propylcarbamoyl)4-methylpentyl]phosphinic acid as a white solid: $^1$HNMR (CD$_3$OD) d 0.83 (d,3H,J=6.9 Hz), 0.89 (d,3H,J=6.9 Hz), 1.02 (s,9H), 1.32 (m,1H), 1.42 (m,1H), 1.53 (m,1H), 1.67

(m,1H), 1.99 (m,1H), 2.69 (s,3H), 2.81 (m,1H), 3.10 (d,2H, J=17.1 Hz), 3.94 (s,2H), 4.08 (s,1 H), 7.1–7.3 (m,9H); mass spectrum m/e: 501 M⁺+H⁺; HPLC retention time: 12.96 minutes; and 208 mg of R,S (4-benzylbenzyl)[2-(2,2-dimethyl-1-methyl carbamoylpropylcarbamoyl)-4-methylpentyl]phosphinic acid as a white solid: $^1$HNMR (CD$_3$OD) d 0.86 (d,3H,J=6.9 Hz), 0.91 (d,3H,J=6.9 Hz), 1.02 (s,9H), 1.22 (m,1H), 1.4–1.7 (m,3H), 2.00 (m,1H), 2.64 (s,3H), 2.85 (m,1H), 3.10 (d,2H,J=17.1 Hz), 3.94 (s,2H), 4.13 (s,1H), 7.1–7.3 (m,9H); mass spectrum m/e: 501 M⁺+H⁺; HPLC retention time: 15.84 minutes.

The compounds in Table 7 were separated by a method analogous to that described in Example 79.

TABLE 7

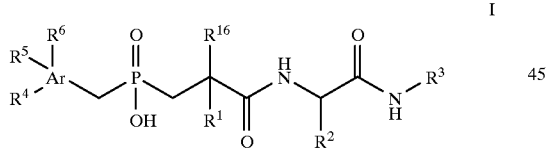

| EX | R$^1$ | R$^2$ | R$^{12}$ | R$^{13}$ | R$^{14}$ | R$^1$ S/R | Ret. Time | MS |
|---|---|---|---|---|---|---|---|---|
| 80 | isobutyl | tert-butyl | H | H | benzyl | 0/100 | —/15.84 | CI: 501 M⁺ + H⁺ |
| 81 | isobutyl | tert-butyl | H | H | benzyl | 100/0 | 12.96/— | CI: 501 M⁺ + H⁺ |
| 82 | isobutyl | tert-butyl | H | H | 3-fluorobenzyl | 100/0 | 13.54/— | CI: 519 M⁺ + H⁺ |
| 83 | isobutyl | tert-butyt | H | H | 3-fluorobenzyl | 0/100 | —/16.20 | CI: 519 M⁺ + H⁺ |
| 84 | 3,3,3-trifluoropropyl | tert-butyl | H | H | benzyl | 100/0 | 13.38/— | CI: 540 M⁺ 541 M⁺ + H⁺ |
| 85 | 3,3,3-trifluoropropyl | tert-butyl | H | H | benzyl | 0/100 | —/15.16 | CI: 540 M⁺ 541 M⁺ + H⁺ |

I claim:
1. A compound of the formula

I or a pharmaceutically acceptable salt thereof; wherein
Ar is phenyl;
R$^1$ and R$^{16}$ are each independently hydrogen, (C$_1$–C$_6$)alkyl, (trifluoromethyl)$_2$(C$_1$–C$_6$)alkyl, perfluoro(C$_1$–C$_6$)alkyl, perfluoro(C$_1$–C$_6$)alkyl(C$_1$–C$_6$)alkyl, difluoromethoxy, trifluoromethoxy, (C$_3$–C$_7$)cycloalkyl (C$_1$–C$_6$)alkyl, (C$_6$–C$_{10}$)aryl(C$_1$–C$_6$)alkyl, (C$_6$–C$_{10}$)aryloxy(C$_1$–C$_6$)alkyl or (C$_6$–C$_{10}$)aryl(C$_1$–C$_6$)alkoxy(C$_1$–C$_6$)alkyl;
R$^2$ is (C$_1$–C$_6$)alkyl or (C$_6$–C$_{10}$)aryl(C$_1$–C$_6$)alkyl optionally substituted by hydroxy, amino, halo, (C$_1$–C$_6$)alkyl, (C$_1$–C$_6$)alkoxy, (trifluoromethyl)$_2$(C$_1$–C$_6$)alkyl, perfluoro(C$_1$–C$_6$)alkyl, perfluoro(C$_1$–C$_6$)alkyl(C$_1$–C$_6$) alkyl, difluoromethoxy, trifluoromethoxy, carboxy or carboxamoyl;
R$^3$ is (C$_1$–C$_6$)alkyl or (C$_6$–C$_{10}$)aryl;
R$^4$ is hydrogen, (C$_1$–C$_6$)alkyl, (C$_1$–C$_6$)alkoxy, (C$_3$–C$_7$)cycloalkyl(C$_1$–C$_6$)alkyl, (C$_1$–C$_6$)alkylsulfonyl, (C$_6$–C$_{10}$)aryl, (C$_6$–C$_{10}$)aryloxy, (C$_6$–C$_{10}$)arylsulfonyl, (C$_6$–C$_{10}$)aryl(C$_1$–C$_6$)alkyl, (C$_6$–C$_{10}$)aryl(C$_1$–C$_6$)alkoxy, (C$_6$–C$_{10}$)aryl(C$_1$–C$_6$)alkylsulfonyl, N-phthalimido, (C$_6$–C$_{10}$)arylNHCO, (C$_6$–C$_{10}$)arylNHSO$_2$, R$^7$OOC, R$^7$R$^8$NCO, R$^7$R$^8$NSO$_2$ wherein R$^7$ and R$^8$ are each independently hydrogen, (C$_1$–C$_6$)alkyl or (C$_6$–C$_{10}$)aryl(C$_1$–C$_6$)alkyl; (C$_1$–C$_6$)alkyl CR$^9$R$^{10}$, (C$_6$–C$_{10}$)aryl CR$^9$R$^{10}$, (C$_6$–C$_{10}$)aryl(C$_1$–C$_6$)alkylCR$^9$R$^{10}$ wherein R$^9$ and R$^{10}$ are each independently fluoro, (C$_1$–C$_6$)alkyl or (C$_1$–C$_6$)alkoxy;
or R$^9$ and R$^{10}$ may be taken together with the carbon to which they are attached to form a group of the formula

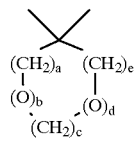

wherein
a is 0, 1 or 2;
b is 0 or 1;
c is 1, 2, or 3;
d is 0 or 1; and
e is 0, 1 or 2;
R$^5$ and R$^6$ are each independently hydrogen, (C$_1$–C$_6$)alkyl, (C$_1$–C$_6$)alkoxy, halo, (trifluoromethyl)$_2$(C$_1$–C$_6$)alkyl, perfluoro(C$_1$–C$_6$)alkyl, perfluoro(C$_1$–C$_6$)alkyl(C$_1$–C$_6$)alkyl, difluoromethoxy, trifluoromethoxy, (C$_1$–C$_6$)alkylthio, (C$_1$–C$_6$)alkylsulfinyl or (C$_1$–C$_6$)alkylsulfonyl;
or R$^1$ and R$^{16}$ may be taken together with the carbon to which they are attached to form a (C$_3$–C$_7$)cycloalkyl group optionally substituted by (C$_1$–C$_6$)alkyl, (C$_1$–C$_6$)alkoxy, (C$_6$–C$_{10}$)aryl(C$_1$–C$_6$)alkyl, (C$_6$–C$_{10}$)aryl (C$_1$–C$_6$)alkyl or (C$_6$–C$_{10}$)aryloxy;
or R$^5$ and R$^6$, when attached to adjacent carbon positions, may be taken together to form a group of the formula

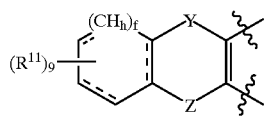

wherein the broken lines represent optional double bonds;

h is 1 or 2;

f and g are each independently 0, 1 or 2;

Y and Z are each independently $CH_2$, O, CO, $SO_2$, $CH_2CH_2$, $CH_2O$, $CH_2S$, $CH_2NH$, $CH_2CO$, $CH_2SO_2$, NHCO or $NHSO_2$; and $R^{11}$ is hydrogen, halo, $(C_1-C_6)$alkyl, $(C_1-C_6)$alkoxy, (trifluoromethyl)$_2(C_1-C_6)$alkyl, perfluoro$(C_1-C_6)$ alkyl, perfluoro$(C_1-C_6)$alkyl$(C_1-C_6)$alkyl, difluoromethoxy or trifluoromethoxy;

with the proviso that when either a or e is 0, the other must be 1;

with the proviso that when b and d are 1, the sum of a, c and e cannot be 5, 6 or 7;

with the proviso that when b and d are 0, the sum of a, c and e cannot be 7;

with the proviso that the methylene carbon attached to the phosphorus atom must be attached to a carbon atom of the Ar ring; and with the proviso that $R^5$ and $R^6$ must be attached to carbon atoms of the Ar ring.

2. A compound according to claim 1, wherein $R^1$ is 2-methylpropyl, trifluoromethylethyl, cyclopropylmethyl, cyclobutylmethyl, phenoxybutyl, cyclohexylmethyl or phenylethyl.

3. A compound according to claim 1, wherein $R^2$ is $(C_1-C_6)$alkyl or 4-methoxybenzyl.

4. A compound according to claim 1, wherein $R^3$ is methyl.

5. A compound according to claim 1, wherein $R^4$ is hydrogen, benzyl, 2-chlorobenzyl, 2-fluorobenzyl, 3-fluorobenzyl or 4-fluorobenzyl.

6. A compound according to claim 1, wherein $R^1$ is 2-methylpropyl, trifluoromethylethyl, cyclopropylmethyl, cyclobutylmethyl, phenoxybutyl, cyclohexylmethyl or phenylethyl; $R^2$ is $(C_1-C_6)$alkyl or 4-methoxybenzyl; $R^3$ is methyl and $R^4$ is hydrogen, benzyl, 2-chlorobenzyl, 2-fluorobenzyl, 3-fluorobenzyl or 4-fluorobenzyl.

7. A compound according to claim 1, wherein said compound is selected from the group consisting of:

(4-Benzylbenzyl)-[2-(2,2-dimethyl-1-methylcarbamoyl-propylcarbamoyl)-4-methyl-pentyl]-phosphinic acid;

(4-Benzylbenzyl-[2-(2,2-dimethyl-1-methylcarbamoyl-propylcarbamoyl)-5,5,5-trifluoropentyl]-phosphinic acid;

[2-(2,2-Dimethyl-1-methylcarbamoyl-propylcarbamoyl)-4-methylpentyl]-[4-(3-fluorobenzyl)-benzyl]-phosphinic acid;

Benzyl-{2-[2-(4-methoxyphenyl)-1-methylcarbamoyl-ethylcarbamoyl]-6-phenoxy-hexyl}-phosphinic acid;

(4-Benzylbenzyl)-{2-[2-(4-methoxyphenyl)-1-methylcarbamoyl-ethylcarbamoyl]-6-phenoxyhexyl}-phosphinic acid;

(4-Benzylbenzyl)-{3-cyclohexyl-2-[2-(4-methoxyphenyl)-1-methylcarbamoyl-ethylcarbamoyl]-propyl}-phosphinic acid;

(4-Benzylbenzyl)-[3-cyclohexyl-2-(2,2-dimethyl-1-methylcarbamoyl-propylcarbamoyl)-propyl]-phosphinic acid;

(4-Benzylbenzyl)-[2-(2,2-dimethyl-1-methylcarbamoyl-propylcarbamoyl)-4-phenyl-butyl]-phosphinic acid;

(4-Cyclohexylmethylbenzyl)-[2-(2,2-dimethyl-1-methylcarbamoyl-propylcarbamoyl)-4-methyl-pentyl]-phosphinic acid;

[2-(2,2-Dimethyl-1-methylcarbamoyl-propylcarbamoyl)-4-methylpentyl]-(4-isobutylbenzyl)-phosphinic acid;

[2-(2,2-Dimethyl-1-methylcarbamoyl-propylcarbamoyl)-4-methylpentyl]-[4-(4-fluoro-benzyl)-benzyl]-phosphinic acid;

[2-(2,2-Dimethyl-1-methylcarbamoyl-propylcarbamoyl)-4-methylpentyl]-[4-(2-fluoro-benzyl)-benzyl] phosphinic acid;

(4-Benzylbenzyl)-{2-[2-(4-methoxyphenyl)-1-methylcarbamoyl-ethylcarbamoyl]-4-methyl-pentyl}-phosphinic acid;

[4-(2-Chlorobenzyl)benzyl]-[2-(2,2-dimethyl-1-methylcarbamoyl-1-propylcarbamoyl)-4-methylpentyl]phosphinic acid;

[2-(2,2-Dimethyl-1-methylcarbamoyl-propylcarbamoyl)-5,5,5-trifluoro-pentyl]-[4-(2-fluoro-benzyl)-benzyl] phosphinic acid;

[3-Cyclopropyl-2-(2,2-dimethyl-1-methylcarbamoyl-propylcarbamoyl)-propyl]-[4-(2-fluoro-benzyl)-benzyl]phosphinic acid; and

[3-Cyclobutyl-2-(2,2-dimethyl-1-methylcarbamoyl-propylcarbamoyl)-propyl]-[4-(2-fluoro-benzyl)-benzyl]-phosphinic acid.

8. A pharmaceutical composition for (a) the treatment of a condition selected from the group consisting of arthritis, cancer, synergy with cytotoxic anticancer agents, tissue ulceration, mucular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 effective in such treatment and a pharmaceutically acceptable carrier.

9. A method for the inhibition of (a) matrix metalloproteinases or (b) the production of tumor necrosis factor (TNF) in a mammal, including a human, comprising administering to said mammal an effective amount of a compound of claim 1.

10. A method for treating a condition selected from the group consisting of arthritis, cancer, synergy with cytotoxic anticaner agents, tissue ulceration, macular degeneration, restenosis, periodontal disease, epidermolysis bullosa, scieritis, in combination with standard NSAID'S and analgesics and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1, effective in treating such a condition.

* * * * *